US005612224A

United States Patent [19]

O'Brien

[11] Patent Number: 5,612,224
[45] Date of Patent: Mar. 18, 1997

[54] METHOD FOR MEASURING THE QUANTITY OF LEAD ON THE SURFACE OF A BRASS COMPONENT

[75] Inventor: Timothy J. O'Brien, Bay Village, Ohio

[73] Assignee: 21st Century Companies, Inc., Tyler, Tex.

[21] Appl. No.: 567,752

[22] Filed: Dec. 5, 1995

Related U.S. Application Data

[63] Continuation-in-part of Ser. No. 391,447, Feb. 21, 1995, abandoned.

[51] Int. Cl.$^6$ .................................................. C12P 19/64
[52] U.S. Cl. .................................... 436/73; 73/53.01
[58] Field of Search ........................... 436/77, 73, 175, 436/178; 73/53.01

[56] References Cited

U.S. PATENT DOCUMENTS

| | | | |
|---|---|---|---|
| 4,786,604 | 11/1988 | Michael | 436/77 |
| 4,873,197 | 10/1989 | Gould | 436/77 |
| 5,019,516 | 5/1991 | Wiese | 436/77 |
| 5,278,075 | 1/1994 | Stone | 436/73 |

Primary Examiner—Hezron E. Williams
Assistant Examiner—Jay L. Politzer
Attorney, Agent, or Firm—Dorn, McEachran, Jambor & Keating

[57] ABSTRACT

A process for measuring the quantity of lead on the waterway surface of a brass component, for example a brass plumbing fixture, includes the steps of filling the brass component waterway with an aqueous solution of an acid which removes lead from the surface of the brass component. The acid solution is removed from the waterway after a time period which is sufficient to remove substantially all surface lead from the brass component, but which is insufficient for the acid to remove significant surface zinc and copper to expose surface lead. The quantity of lead per unit surface area of the brass component can then be determined by the use of the volume of the acid solution, the surface area of the brass component and the concentration of lead in the acid solution.

13 Claims, 2 Drawing Sheets

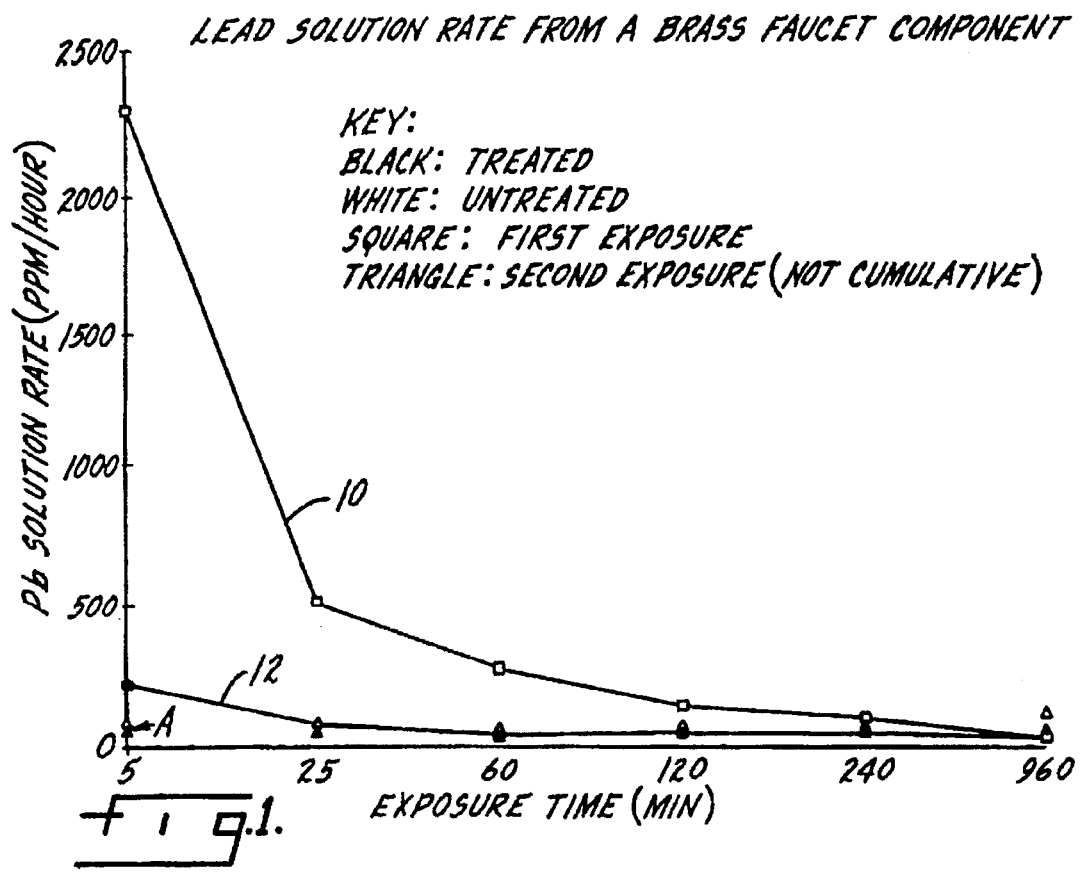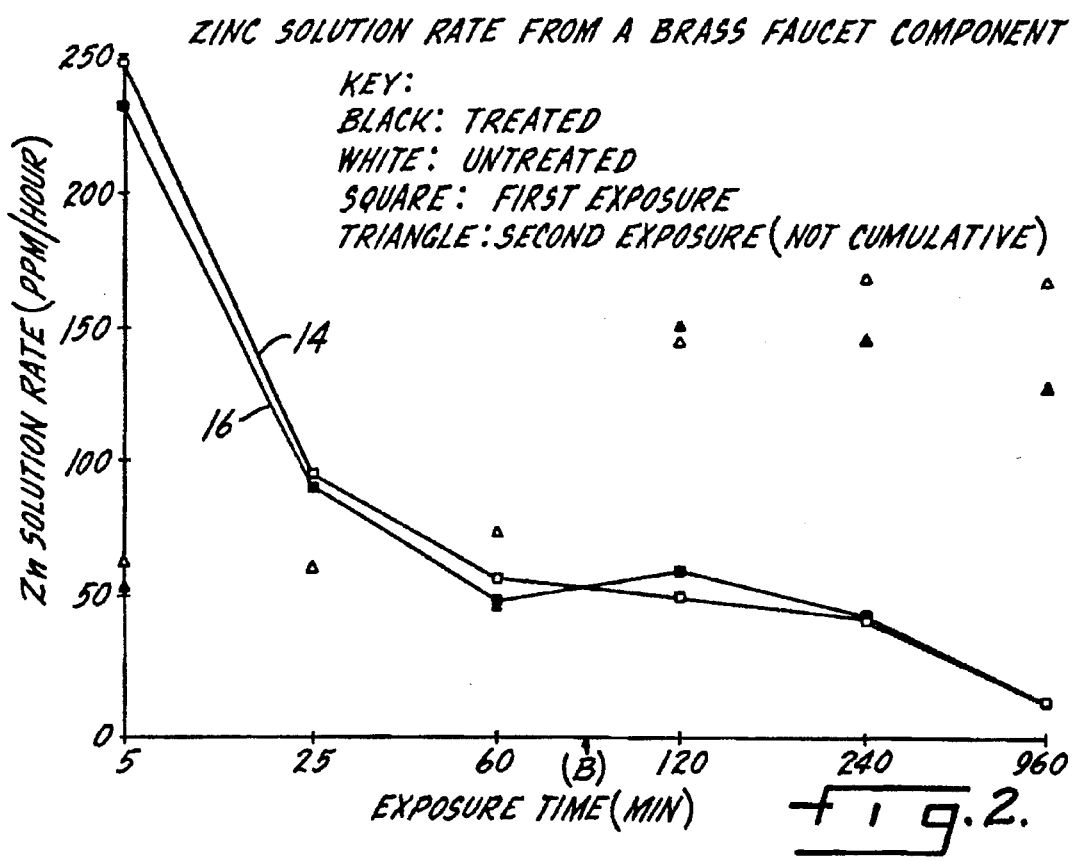

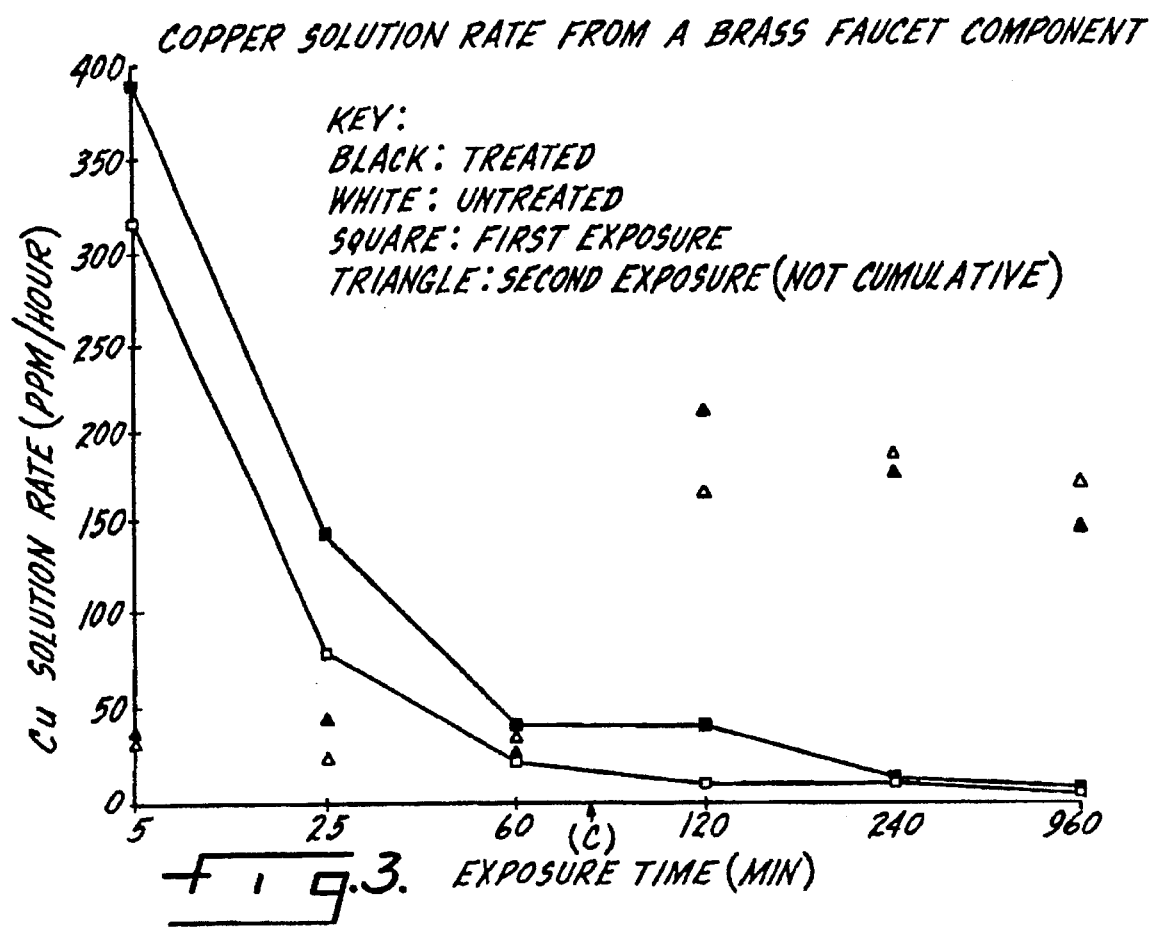
Fig. 3. COPPER SOLUTION RATE FROM A BRASS FAUCET COMPONENT
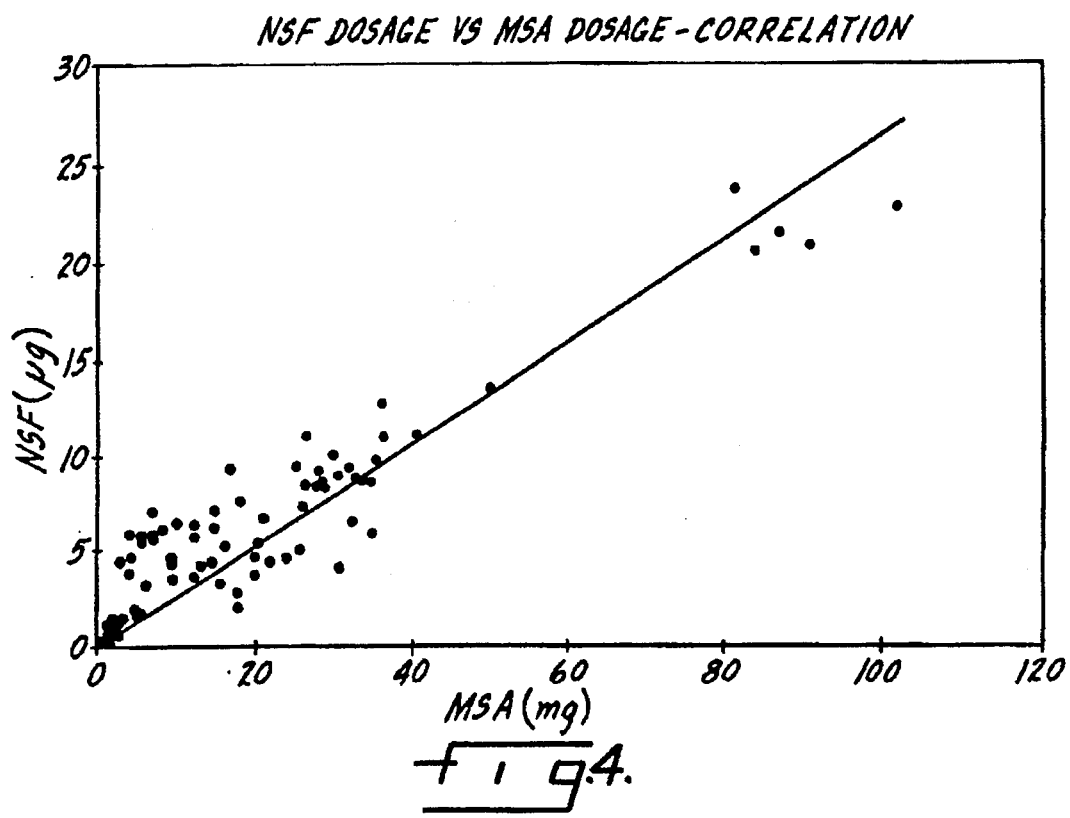
Fig. 4. NSF DOSAGE VS MSA DOSAGE - CORRELATION

METHOD FOR MEASURING THE QUANTITY OF LEAD ON THE SURFACE OF A BRASS COMPONENT

This is a continuation-in-part of application Ser. No. 08/391,447, filed Feb. 21, 1995 now abandoned.

THE FIELD OF THE INVENTION

Leaded brass has been used in the manufacture of water flow fixtures such as shower heads, faucets, tub spouts and the like since such devices first came into modern use. The Environmental Protection Agency (EPA) has issued regulations which limit the maximum quantity of lead that is permitted to be leached into the water from such plumbing fixtures during an overnight dwell or extensive period of non-use. Most faucets presently in use will meet the maximum leachable lead limits established by the EPA prior to 1993. However, the EPA is now reducing the maximum permissible limits, and it is widely anticipated that by the end of 1994 many faucet products currently in production will not meet the revised limits. Consequently, most of the manufacturers of water flow devices such as faucets are expending substantial effort in the redesign of their products or their manufacturing processes to meet the anticipated EPA guidelines for leachable lead.

The EPA has delegated to the National Sanitation Foundation responsibility to develop the protocol which will determine the quantity of lead leaching into the potable water supply by regulated devices such as faucets. It is anticipated that the protocol will evaluate the lead leached into the water supply during the first 19 days after installation, and that on average, faucets will be required to contribute less than 11 micrograms of lead per liter of water to the water sampled after filling and testing according to the precisely defined procedure. This procedure is defined in a document known as the NSF-61 standard. The NSF-61 standard applies to the faucet body and thus the surface area of a particular faucet body is not relevant.

Because the NSF-61 standard requires a 19-day time span for testing and requires multiple chemical analyses per specimen, it is expensive and essentially impractical for the manufacturers of plumbing fittings made of brass to use the NSF-61 protocol as a manufacturing process control tool. The present invention provides a substantially simplified and much less expensive process for measuring the quantity of lead on the surface of a brass component, which quantity has a direct correlation with the quantity of lead which will be leached into the potable water supply over the 19-day period of the NSF-61 protocol.

The process involves filling the brass plumbing fitting waterway with an aqueous solution of an acid which removes lead from the exposed internal surface of the brass component. The solution remains in the waterway for a time period which is sufficient to remove substantially all surface lead from the exposed area, but leaves the zinc and copper substantially unaffected. The concentration of lead in the acid solution is then measured, and from this measurement the quantity of lead on the waterway surface of the brass component can be determined. There is a direct correlation between the quantity of lead so measured and the lead which will be leached from the filling waterway into the potable water supply and thus the measured quantity of lead has a direct relationship with whether or not the particular product will meet the NSF-61 standard.

SUMMARY OF THE INVENTION

The present invention relates to a process for measuring the quantity of lead on the waterway surface of a brass component and specifically the use of such measurement to determine whether the brass component will comply with the National Sanitation Foundation requirements for leachable lead.

One purpose of the invention is a process as described which uses an acid in solution to remove surface lead from the brass component, with the measurement of the removed lead being directly determinative of the quantity of lead which will be leached by that product into the potable water supply over a predetermined time period.

Another purpose is a process as described in which the brass component remains in the acid aqueous solution for a time period sufficient to remove substantially all surface lead, but insufficient for the acid to remove significant surface zinc and copper to expose subsurface lead.

Another purpose of the invention is to provide a simplified inexpensive process for determining the quantity of lead on the surface of a brass component, which determination is directly relevant to the quantity of lead which will be leached by such a brass plumbing fixture into the potable water supply over the period of the National Sanitary Foundation test protocol.

Another purpose is a process to determine the relationship between optimum acid exposure time and plumbing fixture geometry for the use described.

Other purposes will appear in the ensuing specification, drawings and claims.

BRIEF DESCRIPTION OF THE DRAWINGS

The invention is illustrated diagrammatically in the following drawings wherein:

FIG. 1 is a chart illustrating the relationship between exposure time and the rate at which lead dissolves from the surface of a brass component into an acid solution;

FIG. 2 is a chart illustrating the relationship between exposure time and the rate at which zinc dissolves from the surface of a brass component into an acid solution;

FIG. 3 is a chart, similar to FIG. 2, illustrating the relationship between exposure time and the rate at which copper dissolves from the surface of a brass component into an acid solution; and FIG. 4 is a chart illustrating the correlation between the quantity of lead which will be leached by a brass component as determined by the NSF-61 protocol and the quantity of lead dissolved from an identical brass component when exposed to an MSA solution.

DESCRIPTION OF THE PREFERRED EMBODIMENT

The present invention relates to a process for measuring the quantity of lead on the waterway surface of a brass component such as a brass plumbing fixture which may be a shower head, faucet, tub spout or the valve for controlling water flow through such devices. The quantity of lead on the waterway surface of a brass component has a direct relationship with the quantity of lead which will be leached by that component into the potable water supply. It is anticipated that the NSF-61 protocol will limit the quantity of lead which can be leached into the potable water supply over an eleven-day period to 11 micrograms. For plumbing manufacturers to comply with this standard, there must be tight quality control of the manufacturing processes. Because the NSF-61 standard requires testing over a period of 19 days and requires nine separate chemical analyses per specimen, this protocol is too expensive and cumbersome for manufacturing control. The present invention provides a simplified process for measuring the quantity of lead on the surface of a brass component and thus a simplified process for determining if a brass plumbing fixture meets the NSF-61 standard.

In the preferred process, the waterway of the brass component will be filled with an aqueous solution of methane sulfonic acid (MSA) at a concentration of 65 percent by weight for a time period of between 25 minutes and two hours. One hour is the preferred time. The concentration of lead in the acid, after the acid is decanted, is determined by well known chemical analytical techniques, e.g., atomic absorption spectrophotometry. Once the concentration of lead in the acid is known, the quantity of lead can then be calculated from the acid volume and the lead concentration in solution. As the NSF-61 protocol is applied to a faucet body, the actual surface area of the body exposed to the acid is not relevant. What is important is the amount of lead per brass component.

The chart of FIG. 1 illustrates the removal or dissolution of lead from the surface of a brass lavatory faucet in a solution of 65 percent by weight MSA. Each data point represents the average rate at which lead was removed from a test specimen over the designated time period. The curve labeled 10 connects data points for faucet bodies which have had no previous lead removal treatment. It is clear that after 25 minutes in solution, the rate of lead loss from the lead bearing faucets is almost the same as that from similar faucets, represented by curve 12, which have been previously treated by a lead removal process which is described in U.S. Pat. No. 5,454,876. It should be noted from the chart of FIG. 1 that after two hours both the untreated and the deleaded faucet are losing lead at substantially the same rate. The conclusion drawn from this experimental data is that the time period during which the untreated faucet or plumbing fixture body should remain in the MSA solution is between 25 minutes and two hours, as substantially all of the surface lead will be removed during this time period. It is also clear from FIG. 1 that during the first five minutes of exposure to the MSA solution, lead dissolves rapidly if the sample has surface lead, whereas, if the sample has been previously deleaded to remove surface lead, then the rate of lead removed into solution is substantially less rapid.

The chart of FIG. 1 also shows data points for the faucet bodies of curves 10 and 12 which are each given a second exposure of one hour to the same solution. The rate of lead removed during the second exposure is minimal and substantially constant, reinforcing the conclusion that substantially all of the surface lead was removed in the initial exposure. This rate is illustrated on FIG. 1 by the designation (A) and shall herein be referred to as the "background" rate of lead dissolution.

It is important in any such process that the principal components of brass, zinc and copper not be removed or dissolved into solution, as to do so will expose subsurface lead, rendering the process inaccurate and unreliable. Thus, the time period during which the brass plumbing fixture remains in the MSA solution must be such as to maintain the dissolution of copper and zinc at acceptable levels so as to not expose subsurface lead. In the chart of FIG. 2 the data points for curve 14 show the zinc solution rate for untreated brass faucet bodies of the same type as used in the FIG. 1 analysis and the data points for curve 16 show the zinc solution rate for the same type of faucet bodies after a deleading treatment. It should be noted that the zinc solution rate is substantially the same for both in the first solution exposure. The data points for the second solution exposure of the same faucet bodies show that in a time period between one and two hours the MSA begins to attack the zinc more rapidly. The relatively sudden onset of more rapid zinc dissolution shall be referred to herein as "breakaway" for zinc. The breakaway point for zinc is illustrated on FIG. 2 by the designation (B). The breakaway point for copper is illustrated on FIG. 3 by the designation (C). As zinc loss is undesirable because ultimately it will lead to further exposure of subsurface lead, the experimental data of FIG. 2 illustrates the maximum time in solution should be no greater than two hours.

The chart of FIG. 3, similar to that of FIG. 2, shows the rate of copper dissolving into solution is substantially the same as that for zinc and with a concurrent time period.

There is a relationship between micrograms of lead leached into the potable water supply as determined by the NSF-61 protocol and the milligrams of lead in the MSA acid solution after the brass component or plumbing fixture has been exposed to the solution for the preferred time period of one hour. This relationship is illustrated graphically in FIG. 4 in which the data points represent a range of leaded brass receptacles similar in geometry to commercially available faucet bodies. Based on this relationship, it is determined that the micrograms of lead which would be leached into water pursuant to the NSF-61 protocol is equal to a constant number, 0.26, times the milligrams of lead in the MSA solution. Thus, in terms of a manufacturing process control, a brass plumbing fitting or fixture can be immersed in the MSA solution described for the preferred time of one hour, the lead in solution then determined which will give a predictable indication if the lead on the surface of that brass plumbing fitting will or will not result in that product meeting the NSF-61 protocol.

The invention should not be limited to the use of MSA as the solvent extraction acid. Other acids may also be useful and particularly an acid 2-ethyl-hexyl phosphoric acid (EHPA) dissolved in kerosene. The technique using EHPA would be similar to that described with MSA, as again the intent is to dissolve surface lead into solution without dissolving unacceptable amounts of copper and zinc which would expose subsurface lead.

Based on the experimental data illustrated by the charts of FIGS. 1–4, it is possible to provide a manufacturing process control for brass plumbing fixtures which may have been pretreated to remove surface lead, with the process control using the described acid bath to measure the quantity of surface lead. This measurement may then indicate directly whether or not the treated component will comply with the NSF-61 protocol.

The experimental data further provides a basis to determine the optimum waterway exposure time for various types of plumbing fixtures. Waterway geometry will vary for different plumbing fixtures which dictates different solution exposure times to determine whether or not the plumbing fixture complies with the NSF-61 protocol. The present invention provides a process to determine optimum exposure time which includes the steps of: treating the brass fixture with the described acid for a variable time, as illustrated by the charts in FIGS. 1, 2 and 3, and then analyzing the lead, copper and zinc content in the resultant solution; retreating the same fixture with a fixed time exposure and analyzing the lead, copper and zinc content in the resultant solution; and finally plotting the lead, copper and zinc content against solution process time and determining the point at which the second exposure curves show no additional lead above background (A) and the point (C) beyond which breakaway occurs (increased copper and zinc) causing exposure of new subsurface lead. The optimal exposure time is then longer than the time taken to reach (A) and shorter than the time taken to reach (B) or (C).

Whereas the preferred form of the invention has been shown and described herein, it should be realized that there may be many modifications, substitutions and alterations thereto.

The embodiments of the invention in which an exclusive property or privilege is claimed are defined as follows:

1. A process for measuring the quantity of lead on the waterway surface of a brass component including the steps of:

filling the brass component waterway with an aqueous solution of an acid which removes lead from the surface of the brass component, removing the acid solution from brass component waterway after a time period which is sufficient to remove substantially all surface lead from the brass component, which time period is insufficient for the acid to remove significant surface zinc and copper from the brass component to expose subsurface lead, measuring the concentration of lead in the acid solution, and determining the quantity of lead removed from the brass component by means of the volume of acid solution and the concentration of lead in the acid solution after removal from the brass component.

2. The process of claim 1 characterized in that the acid solution contains methane sulfonic acid.

3. The process of claim 2 characterized in that the methane sulfonic acid is in solution at a concentration of 65 percent by weight.

4. The process of claim 1 characterized in that the aqueous solution remains in contact with the brass component for a time period of between 25 minutes and two hours.

5. The process of claim 4 characterized in that the aqueous solution remains in contact with the brass component for approximately one hour.

6. The process of claim 1 characterized in that the brass component is a plumbing fixture.

7. A process for determining the total quantity of lead leachable into potable water over a predetermined time period from a brass plumbing fixture including the steps of:

maintaining the brass plumbing fixture filled with water for a predetermined time period and measuring the resultant quantity of lead, A, leached into the water by a predetermined test protocol, filling the brass plumbing fixture with an aqueous solution of an acid which removes lead from the surface of the brass plumbing fixture, removing the aqueous solution from the brass plumbing fixture after a time period which is sufficient to remove substantially all surface lead from the brass plumbing fixture, which time period is insufficient for the acid to remove significant surface zinc and copper from the brass plumbing fixture to expose subsurface lead, measuring the concentration of lead in the acid solution, determining the total quantity of lead, B, leachable into potable water from the brass plumbing fixture during the predetermined time period by means of the volume of acid solution and the concentration of lead in the acid solution, and establishing a mathematical correlation between A and B.

8. The process of claim 7 characterized in that the acid solution contains methane sulfonic acid.

9. The process of claim 8 characterized in that the methane sulfonic acid is in solution at a concentration of 65 percent by weight.

10. The process of claim 7 characterized in that the test protocol is the NSF-61 protocol.

11. The process of claim 7 characterized in that the brass plumbing fixture is exposed to the aqueous solution for a time period of between 25 minutes and two hours.

12. The process of claim 11 characterized in that the brass plumbing fixture is exposed to the aqueous solution for approximately one hour.

13. A process to determine the optimum exposure time for a brass plumbing fixture immersion in an acid solution, including the steps of:

treating the brass fixture with acid for a variable time and analyzing the lead, copper and zinc content of the resultant solution;

retreating the same fixture with a fixed time exposure to acid and analyzing the lead, copper and zinc content of the resultant solution; and plotting lead, copper and zinc content against process time and determining the point at which the second exposure curves show no additional lead above background and the inflection point beyond which breakaway occurs (increased copper and zinc) causing exposure of new subsurface lead.

* * * * *